(12) United States Patent
MacMeccan et al.

(10) Patent No.: US 8,460,698 B2
(45) Date of Patent: *Jun. 11, 2013

(54) COMPOSITE ARTICLE SUITABLE FOR USE AS A WOUND DRESSING

(75) Inventors: Robert M. MacMeccan, Greer, SC (US); Le Zhang, Spartanburg, SC (US); Keith A. Keller, Spartanburg, SC (US); Martin E. Cowan, Moore, SC (US); T. Andrew Canada, Chesnee, SC (US)

(73) Assignee: Milliken & Company, Spartanburg, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 12/497,138

(22) Filed: Jul. 2, 2009

(65) Prior Publication Data

US 2010/0030178 A1 Feb. 4, 2010

Related U.S. Application Data (60) Provisional application No. 61/173,794, filed on Apr. 29, 2009, provisional application No. 61/085,596, filed on Aug. 1, 2008.

(51) Int. Cl.
*A61K 33/42* (2006.01)
(52) U.S. Cl.
USPC ............... 424/445; 424/604; 442/123
(58) Field of Classification Search
None
See application file for complete search history.

(56) References Cited

U.S. PATENT DOCUMENTS

| 3,459,618 | A | 8/1969 | Egler |
| 4,073,993 | A | 2/1978 | Lark |
| 4,501,025 | A | 2/1985 | Kuznetz |
| 4,984,570 | A * | 1/1991 | Langen et al. ............. 602/44 |
| 5,312,667 | A | 5/1994 | Lumb et al. |
| 5,547,733 | A | 8/1996 | Rock et al. |
| 5,735,145 | A | 4/1998 | Pernick |
| 5,901,373 | A | 5/1999 | Dicker |
| 6,013,275 | A * | 1/2000 | Konagaya et al. ............ 424/443 |
| 6,160,196 | A | 12/2000 | Knieler et al. |
| 6,180,052 | B1 | 1/2001 | Ouellette et al. |
| 6,194,332 | B1 | 2/2001 | Rock et al. |
| 6,263,707 | B1 * | 7/2001 | Miller et al. ................. 66/171 |
| 6,806,214 | B2 | 10/2004 | Li et al. |
| 6,986,270 | B2 * | 1/2006 | Miller et al. ................. 66/202 |
| 2005/0035327 | A1 * | 2/2005 | Canada et al. ........... 252/182.15 |
| 2005/0256437 | A1 | 11/2005 | Silcock et al. |
| 2006/0148356 | A1 | 7/2006 | Zhang et al. |
| 2007/0166503 | A1 | 7/2007 | Hannigan |
| 2008/0063695 | A1 | 3/2008 | Vitaris |

FOREIGN PATENT DOCUMENTS

| EP | 0 242 415 | A1 | 10/1987 |
| GB | 1 110 016 | | 4/1968 |
| GB | 2 430 443 | A | 3/2007 |
| WO | WO 01/90465 | A2 | 11/2001 |
| WO | WO 01/90465 | A3 | 11/2001 |
| WO | WO 2006/094098 | A2 | 9/2006 |

* cited by examiner

*Primary Examiner* — Hasan Ahmed (74) *Attorney, Agent, or Firm* — Robert M. Lanning (57) ABSTRACT

A composite article comprises a fluid transport layer having first and second surfaces and a hydrophobic layer applied to the first surface of the fluid transport layer. When the composite article is used as a wound dressing, the first surface of the fluid transport layer provides a skin-facing surface. The hydrophobic layer comprises a plurality of discontinuities, and at least a portion of the discontinuities have a dimension sufficient to permit the passage of fluid through the hydrophobic layer and into the fluid transport layer.

22 Claims, 3 Drawing Sheets

COMPOSITE ARTICLE SUITABLE FOR USE AS A WOUND DRESSING

CROSS-REFERENCE TO RELATED APPLICATIONS

This application claims, pursuant to 35 U.S.C. §119(e), the benefit of the filing date of U.S. Patent Application No. 61/085,596, which was filed on Aug. 1, 2008, and the filing date of U.S. Patent Application No. 61/173,794, which was filed on Apr. 29, 2009.

TECHNICAL FIELD OF THE INVENTION

The present invention is directed to composite articles exhibiting unique fluid transport properties. These fluid transport properties make the composite articles particularly suitable for use as wound dressings.

BACKGROUND

In the medical field, it is well-established that many factors affect the speed with which wounds heal. Among those factors, the amount of moisture present at the wound site has been found to be particularly important to the wound healing process. Generally speaking, excessive moisture at the wound site can lead to maceration, undesirable bacterial growth, and excessive protease enzyme activity. This bacterial growth can increase the potential for infection to occur, and the protease enzymes generated can damage tissue at the wound site. Thus, excessive moisture can hamper or delay the wound healing process.

Conversely, insufficient moisture at the wound site can deleteriously affect the wound healing process. Insufficient moisture at the wound site can cause scab or eschar formation and the generation of scar tissue. The formation of such tissues may cause any wound care device or medical dressing in contact with the wound to adhere to the wound. The removal of an adhered device or dressing can cause undue discomfort to the patient and can disrupt granulation tissue at the wound site. The removal of an adhered device or dressing can also leave pieces of the device or dressing imbedded in the wound. The presence of such debris can compound the risk of infection, especially if the wound and/or dressing are already colonized with pathogenic microbes.

A need therefore exists for an article that is suitable for use as a wound dressing and exhibits properties that permit the article to provide an environment suited to the promotion of wound healing. In particular, a need exists for an article that manages fluid (e.g., wound exudates) in such a way as to provide an environment that is sufficiently moist to promote the formation of granulation tissue and other wound-healing structures while also controlling the level of moisture in order to lessen the risk of maceration and the growth or proliferation of undesirable bacteria. The present invention seeks to provide such an article.

BRIEF SUMMARY OF THE INVENTION

In a first embodiment, the invention provides a composite article comprising a fluid transport layer having first and second surfaces and a hydrophobic layer applied to the first surface of the fluid transport layer. The first surface of the fluid transport layer has a first surface energy, and the second surface of the fluid transport layer has a second surface energy. The second surface energy is greater than the first surface energy. The hydrophobic layer has a third surface energy, and the third surface energy is less than the first surface energy. The hydrophobic layer comprises a plurality of discontinuities, and at least a portion of the discontinuities have a dimension sufficient to permit the passage of fluid through the hydrophobic layer and into the fluid transport layer.

In a second embodiment, the invention provides a composite article such as that described in the preceding paragraph further comprising a fluid retentive layer. The fluid retentive layer has a first surface and a second surface. The first surface of the fluid retentive layer has a fourth surface energy, and the fourth surface energy can be greater than the second surface energy. The fluid retentive layer is positioned so that the first surface of the fluid retentive layer is adjacent to the second surface of the fluid transport layer.

In further embodiments, the invention provides composite articles comprising a moisture vapor permeable film. The moisture vapor permeable film generally is positioned so that it is on the surface of the composite article that is farthest removed from the first surface of the fluid transport layer. Thus, depending upon the construction of the composite article, the moisture vapor permeable film can be positioned so that it is adjacent to the second surface of the fluid transport layer or so that it is adjacent to the second surface of the fluid retentive layer.

DETAILED DESCRIPTION OF THE INVENTION

As utilized herein, the term "surface energy" refers to the excess energy at the surface of a material compared to the bulk of the material (e.g., the interior portions of the material) and is usually expressed in terms of millijoules per square meter ($mJ/m^2$). The surface energy quantifies the disruption of intermolecular bonds that occurs when a surface is created. The surface energy can be measured by several means including, for example, the Fowkes method. In this method, two reference liquids are used to first measure the dispersive component and the polar component of the material's surface energy. The surface energy of the material is then calculated from the measured dispersive and polar components. In general, a surface having a higher surface energy will exhibit a higher affinity for aqueous fluids, such as perspiration or wound exudate.

Figure 1:
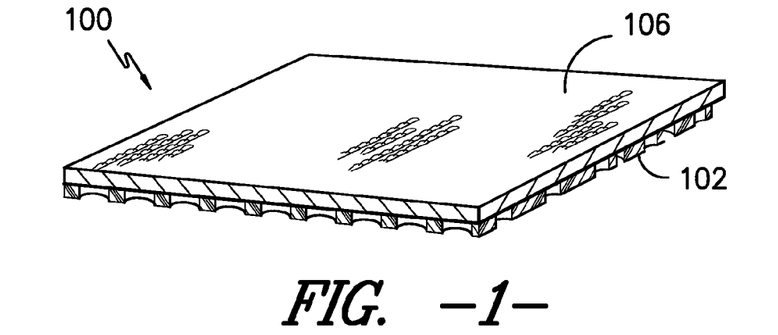
FIG. 1 is a perspective view of a composite article according to the invention.
Figure 1A:
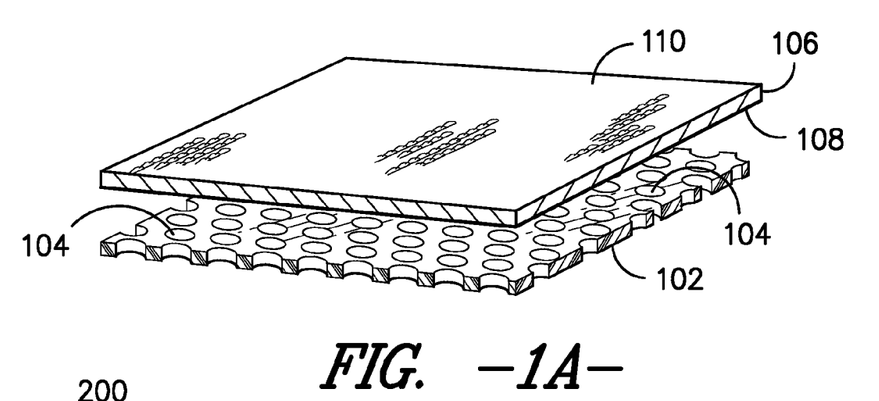
FIG. 1A is an exploded, perspective view of the composite article depicted in FIG. 1.

In a first embodiment, the invention provides a composite article comprising a fluid transport layer and a hydrophobic layer. As depicted in FIG. 1 and FIG. 1A, the composite article 100 comprises a fluid transport layer 106. The fluid transport layer 106 has a first surface 108, which provides a fluid-contacting or skin-facing surface for the composite article 100, and a second surface 110. The hydrophobic layer 102 is applied to the first surface 108 of the fluid transport layer 106.

The fluid transport layer of the composite article can be any suitable material that is capable of absorbing fluids that contact the first surface 108 of the fluid transport layer 106 and transporting or wicking those fluids away from the fluid-contacting surface. In a specific embodiment, the fluid transport layer can be a textile material, such as a textile material selected from the group consisting of knit textiles, woven textiles, and non-woven textiles.

As noted above, the fluid transport layer 106 comprises a first surface 108 and a second surface 110. The first surface 108 of the fluid transport layer 106 has a first surface energy, and the second surface 110 of the fluid transport layer 106 has a second surface energy. In certain embodiments, the surface energy of the first surface 108 of the fluid transport layer 106 and the surface energy of the second surface 110 of the fluid transport layer 106 can be substantially the same. In a specific embodiment, the surface energy of the second surface 110 of the fluid transport layer 106 is greater than the surface energy of the first surface 108 of the fluid transport layer 106. This difference in surface energies between the two surfaces means that the second surface 110 of the fluid transport layer 106 exhibits a greater affinity for aqueous fluids (e.g., perspiration or wound exudates) than the first surface 108 of the fluid transport layer 106. Thus, any aqueous fluids absorbed by the fluid transport layer 106 will be transported or pumped from the first surface 108 to the second surface 110 of the fluid transport layer 106. This active transportation or pumping of the fluids ensures that excess moisture does not accumulate at or near the interface of fluid transport layer 106 and a fluid exuding surface, such as the skin or an exuding wound.

When the fluid transport layer comprises first and second surfaces having different surface energies, the difference between the two surface energies can be of any suitable magnitude. In a specific embodiment, the surface energy of the second surface 110 of the fluid transport layer 106 can be about 101% or more of the surface energy of the first surface 108 of the fluid transport layer 106. In more specific embodiments, the surface energy of the second surface 110 can be about 102% or more, about 103% or more, or about 104% or more of the surface energy of the first surface 108.

In a specific embodiment, the fluid transport layer 106 can be a textile material in which the surface energy of the second surface 110 is higher than the surface energy of the first surface 108. In such an embodiment, the textile material can be selected from the group consisting of knit textiles, woven textiles, and non-woven textiles. Suitable knit textiles include, but are not limited to, weft-knit textiles, such as flat-knit textiles and circular-knit textiles. One embodiment of such a fluid transport layer is depicted in FIG. 2.

Figure 2:
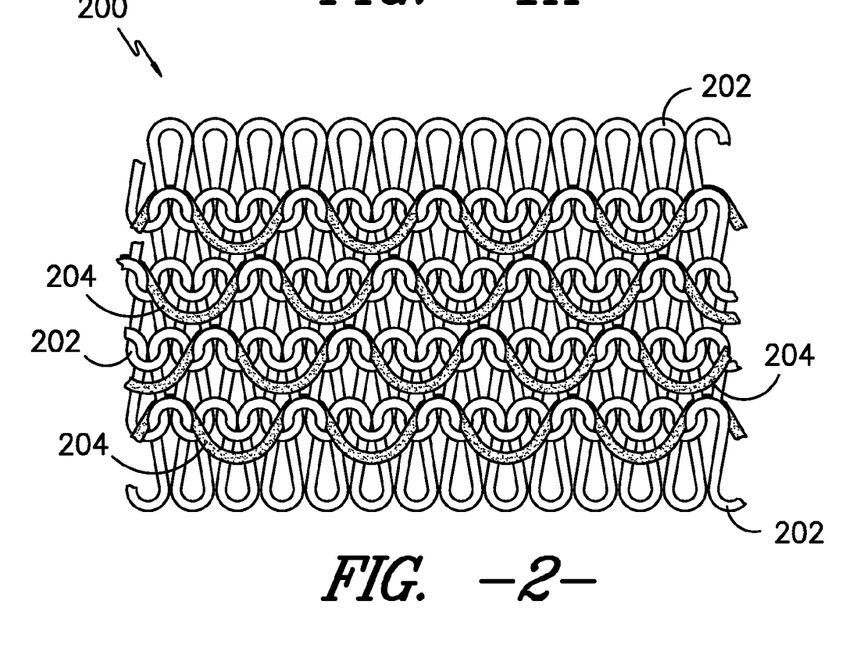
FIG. 2 is a plan view of a laid-in fabric suitable for use as the fluid transport layer of a composite article according to the invention.

As depicted in FIG. 2, the fluid transport layer 200 can be a laid-in fabric comprising one or more yarns 202 providing the knit structure of the fabric and one or more effect yarns 204 tucked into the fabric structure. In order to provide two surfaces having different surface energies, the fluid transport layer 200 depicted in FIG. 2 is a jersey knit fabric in which the effect yarn(s) 204 are incorporated into the fabric structure so that the effect yarn(s) 204 are predominantly present on the technical back of the fabric structure. In other words, the effect yarn(s) 204 are incorporated in the fabric structure so that most of the effect yarn(s) 204 (e.g., most of the surface area of the effect yarn(s)) is present on the technical back of the fabric structure. Such a construction results in a fabric in which the technical face of the fabric is predominantly one type of yarn 202, and the technical back presents a higher proportion of the effect yarn(s) 204. Thus, when the yarn 202 and the effect yarn 204 have different surface energies or one is more hydrophilic than the other, the resulting fabric will exhibit a different surface energy on each of its major surfaces. In a specific embodiment of the fluid transport layer depicted in FIG. 2, the yarn(s) 202 are more hydrophilic than the effect yarn(s) 204. For example, the yarn(s) 202 can be polyamide yarns (e.g., nylon yarns), and the effect yarn(s) 204 can be polyester yarns. Such an embodiment of the fluid transport layer, which is available from Milliken & Company and sold as Dryline® knit fabric, provides a layer in which the technical face of the fabric exhibits a higher surface energy than the technical back of the fabric. Thus, when utilized as the fluid transport layer of the composite article depicted in FIG. 1 and FIG. 1A, such a fabric (i.e., the fabric depicted in FIG. 2) is disposed so that the technical back of the fabric forms the first surface 108 of the fluid transport layer 106 and the technical face of the fabric forms the second surface 110 of the fluid transport layer 106.

A fluid transport layer such as that depicted in FIG. 2 can further comprise yarns or fibers that provide the layer with the ability to be stretched and then return to dimensions that are substantially the same as its original dimensions. For example, in addition to the components noted above, the yarn(s) 202 can further comprise elastomeric fibers, or the fluid transport layer can further comprise elastomeric fibers or yarns that are "parallel" to the yarn(s) 202 (i.e., the elastomeric yarns or fibers are incorporated into the knit structure so that they run alongside the yarn(s) 202). Alternatively, in addition to the effect yarn(s) 204, the fabric can include elastomeric yarn(s) or stretch yarn(s) that have been tucked into the fabric structure. In a specific embodiment, the fluid transport layer comprises an elastomeric yarn, such as a Spandex yarn (i.e., a manufactured fiber in which the fiber-forming substance is a long chain synthetic polymer composed of at least 85% of a segmented polyurethane).

In order to provide the differential surface energies described above, the fluid transport layer can also comprise a material in which one surface or both surfaces have been chemically or physically modified to yield a material having first and second surfaces exhibiting different surface energies. In such an embodiment, the chemical or physical surface treatment can be disposed only on the surface(s) of the fluid transport layer, or the surface treatment can extend beneath the surface(s) of the fluid transport layer and into the interior portions of the layer. However, in either case, the chemical or physical treatment cannot render the modified surface incapable of allowing a fluid (e.g., an aqueous fluid) to wet through. Methods for chemically or physically modifying a surface to change its surface energy are generally known to those of ordinary skill in the art. For example, a textile material can, as described in U.S. Pat. No. 4,073,993 (Lark), be treated with a partial ester compound in such a way as to produce a durable hydrophilic finish on one side of the textile material. Alternatively, a textile material can be treated with ethoxylated or sulfonated polyesters or ethoxylated or sulfonated nylons in such a way as to produce a durable hydrophilic finish on one side of the textile material. For the sake of clarity, it should be noted that the chemical and physical modifications described in this paragraph are used to create a difference in surface energy between the two major surfaces of the fluid transport layer prior to the application of the hydrophobic layer described below. Thus, if such chemical or physical modifications are used to create a difference in surface energy between the surfaces of the fluid transport layer, an additional coating or treatment, such as those described below, is used to create the hydrophobic layer of the composite article.

The fluid transport layer of the composite article can exhibit any suitable absorptive capacity. For example, the fluid transport layer can exhibit a fluid absorption (e.g., water absorption) of about 25 wt. % or more based on the weight of the fluid transport layer. In a specific embodiment, the fluid transport layer can exhibit a fluid absorption (e.g., water absorption) of about 100 wt. % or more, about 150 wt. % or more, about 200 wt. % or more, or about 250 wt. % or more based on the weight of the fluid transport layer.

As noted above, the composite article comprises a hydrophobic layer. As depicted in FIG. 1 and FIG. 1A, the hydrophobic layer 102 is positioned so that it is adjacent to the first surface 108 of the fluid transport layer 106. Thus, as depicted in FIG. 1 and FIG. 1A, the hydrophobic layer provides a fluid-contacting surface for the composite article 100. The hydrophobic layer 102 exhibits a surface energy (i.e., a third surface energy). In order to promote moisture transport through the composite article, the hydrophobic layer 102 preferably exhibits a surface energy that is lower than the surface energy of the first surface 108 of the fluid transport layer 106 (i.e., the hydrophobic layer is more hydrophobic than the first surface of the fluid transport layer). In such an embodiment, the difference in surface energies between the two hydrophobic layer 102 and the first surface 108 of the fluid transport layer 106 means that the first surface 108 of the fluid transport layer 106 exhibits a greater affinity for aqueous fluids (e.g., perspiration or wound exudates) than the hydrophobic layer 102. Thus, any aqueous fluids absorbed by the composite article 100 will be transported or pumped from the hydrophobic layer 102 to the first surface 108 of the fluid transport layer 106. This active transportation or pumping of the fluids ensures that excess moisture does not accumulate at or near the interface of the composite article 100 and a fluid exuding surface, such as the skin or an exuding wound.

The hydrophobic layer can be made from any suitable material. For example, the hydrophobic material can be a discrete layer (e.g., a film) applied to the first surface 108 of the fluid transport layer 106 or a chemical coating or chemical treatment applied to the first surface 108 of the fluid transport layer 106. Thus, as utilized herein, the term "hydrophobic layer" does not necessarily refer to a layer of material that can be physically separated from the fluid transport layer. Rather, the term "hydrophobic layer" is also intended to refer to a region of the composite article exhibiting a lower surface energy than the underlying regions of the first surface of the fluid transport layer (e.g., the underlying regions of the first surface of the fluid transport layer that have not been coated or treated with the chemical). Furthermore, the term "hydrophobic layer" is not intended to suggest or require that the layer or region must be separated from an adjacent portion of the fluid transport layer by a distinct boundary at which the surface energy abruptly changes. The hydrophobic layer can, for example in those embodiments using a chemical coating as described below, penetrate the fluid transport layer and extend below the first surface of the fluid transport layer and partially into the interior of the fluid transport layer. In such an embodiment, the interpenetration of the hydrophobic layer may result in a surface energy gradient, with the surface energy being lowest at the surface of the hydrophobic layer and gradually increasing up to the furthest extent that the hydrophobic coating material penetrated the fluid transport layer. In these embodiments, the surface energy of the first surface of the fluid transport layer can be determined by measuring the surface energy at or beyond the furthest extent to which the hydrophobic coating material penetrated the fluid transport layer. Also, the surface energy of the first surface of the fluid transport layer can be preserved in those areas of the fluid transport layer underlying the discontinuities in the hydrophobic layer, if such discontinuities are present.

Preferably, the hydrophobic layer is made from a material that provides a surface exhibiting a lower surface energy than the first surface of the fluid transport layer. Suitable materials for the hydrophobic layer include, but are not limited to, polymer films (e.g., apertured polymer films), fluorochemical coatings applied to the first surface of the fluid transport layer, hydrophobic, pressure sensitive adhesive coatings applied to the first surface of the fluid transport layer, waxy coatings applied to the first surface of the fluid transport layer, and silicone coatings applied to the first surface of the fluid transport layer. The hydrophobic layer can also be made from combinations of the aforementioned materials, such as a polymeric film (e.g., an apertured polymeric film) to which a fluorochemical, pressure sensitive adhesive, waxy, or silicone coating has been applied.

As noted above, the hydrophobic layer can be a polymer film (e.g., an apertured polymer film), a fluorochemical coating applied to the first surface of the fluid transport layer, a hydrophobic, pressure sensitive adhesive coating applied to the first surface of the fluid transport layer, a waxy coating applied to the first surface of the fluid transport layer, a silicone coating applied to the first surface of the fluid transport layer, a hydrophobic acrylic polymer coating applied to the first surface of the fluid transport layer, a polyvinyl chloride-based coating applied to the first surface of the fluid transport layer, and any combinations thereof. Fluorochemicals suitable for use in making the fluorochemical coating include, but are not limited to, polymers and copolymers having multiple fluorochemical groups (e.g., $C_4$, $C_6$, and $C_8$ fluorochemical groups) attached to the polymer backbone, such as Unidyne S-2029K $C_6$ fluorochemical. The fluorochemicals suitable for use in making the fluorochemical coating can also be in the form of an emulsion or a coating on a carrier, such as fluorochemical coated silica particles from G3 Technology Innovations, LLC. Pressure sensitive adhesives suitable for use in making the hydrophobic, pressure sensitive adhesive coating include, but are not limited to, silicone-based pressure sensitive adhesives, such as the DOW 7800 platinum catalyzed silicone air-cure adhesives (e.g., Uro-bond® III brush-on adhesive from Urocare Products, Inc.), and adhesive silicone films, such as Bioflex Rx1267 silicone gel adhesive from Scapa North America. Silicones suitable for use in making the silicone coating include, but are not limited to, silicone films, such as the 1-50 mil knifecoated silicone films available from Specialty Silicone Fabricators. Waxes or waxy compounds suitable for use in making the waxy coating include, but are not limited to, vegetable waxes (e.g., carnauba wax), animal waxes (e.g., beeswax, insect waxes, and shellac waxes), petroleum waxes (e.g., paraffin wax, microcrystalline wax, and polyethylene wax), mineral waxes (e.g., montan wax and ozokerite), and combinations thereof. Waxy compounds suitable for use in making the waxy coating also include, but are not limited to, higher aliphatic acids (e.g., stearic acid, palmitic acid, and behenic acid), higher alcohols (e.g., stearyl alcohol, palmityl alcohol, and behenyl alcohol), higher aliphatic acid esters (e.g., cetyl palmitate, myricyl palmitate, cetyl stearate, and myricyl stearate), higher amides (e.g., acetamide, propionamide, palmitic acid amide, stearic acid amide, or amide wax), higher amines (e.g., stearylamine and behenylamine), and combinations thereof. Hydrophobic acrylic polymers suitable for use in making the coating applied to the first surface of the fluid transport layer include, but are not limited to, modified acrylic polymers, such as water-reducible, modified acrylic polymers (e.g., No-Tox® water-based inks available from Colorcon®, Inc.). Polyvinyl chloride-based polymers suitable for application to the first surface of the fluid transport layer include, but are not limited to, polyvinyl chloride-based polymers used in plastisol inks. The hydrophobic coating may further comprise surfactants, solvents, catalysts, preservatives, or anti-foaming agents as desired.

In those embodiments in which the hydrophobic layer is a discrete layer (e.g., a film) applied to the first surface 108 of the fluid transport layer 106, the composite article can comprise an adhesive (not depicted) disposed between the hydrophobic layer 102 and the first surface 108 of the fluid transport layer 106. The adhesive can be any suitable material capable of adhering together the hydrophobic layer and the fluid transport layer, provided the adhesive does not deleteriously affect the passage or transport of fluid between the hydrophobic layer and the first surface of the fluid transport layer. Furthermore, in those embodiments of the composite article in which the hydrophobic layer exhibits a surface energy that is lower than the surface energy of the first surface of the fluid transport layer, the adhesive preferably does not affect or disrupt the increasing gradient of surface energies between the hydrophobic layer and the first surface of the fluid transport layer. Suitable adhesives include, but are not limited to, pressure-sensitive adhesives (e.g., discontinuous pressure-sensitive adhesive films), hot-melt adhesives, thermally-cured adhesives, aerobically-cured adhesives, anaerobically-cured adhesives, photocuring adhesives (e.g., ultraviolet light-cured adhesives), and moisture-cured adhesives. In order to permit the passage or transport of fluid between the hydrophobic layer and the first surface of the fluid transport layer, each of these adhesives can be applied in such a way as to create discontinuities in the adhesive layer, such as by patterned application, application in the form of a discontinuous film, application in a form supported by a discontinuous film (e.g., a coating of adhesive on a discontinuous film "carrier"), application in the form of a scrim (e.g., a scrim comprised of fibers made from a hot melt adhesive), or application in a form supported by a scrim (e.g., a scrim comprised of fibers coated with one of the aforementioned adhesives).

In those embodiments in which the hydrophobic layer exhibits a surface energy that is lower than the surface energy of the first surface of the fluid transport layer, the difference in surface energies can be of any suitable magnitude. In certain embodiments, the surface energy of the first surface 108 of the fluid transport layer 106 can be about 101% or more of the surface energy of the hydrophobic layer 102. In more specific embodiments, the surface energy of the first surface 108 of the fluid transport layer 106 can be about 102% or more, about 103% or more, about 104% or more, about 105% or more, about 110% or more, about 115% or more, about 120% or more, or about 125% or more of the surface energy of the hydrophobic layer 102.

In order to ensure that the presence of the hydrophobic layer does not produce a surface that is overly water-repellent, the hydrophobic layer 102 preferably comprises a plurality of discrete discontinuities 104. These discontinuities 104 provide a path for fluid to pass through the hydrophobic layer 102 of the composite article 100 and into the fluid transport layer 106, where the difference in surface energies between the two surfaces of the fluid transport layer 106 then act to transport or pump the fluid through the fluid transport layer 106 and away from the fluid-contacting surface of the composite article 100.

The discontinuities in the hydrophobic layer can have any suitable dimension(s). Preferably, at least a portion of the discontinuities have a dimension sufficient to permit the passage of fluid through the hydrophobic layer and into the fluid transport layer. For example, in certain embodiments, the hydrophobic layer can comprise a plurality of discontinuities having a dimension of from about 7 µm to about 3,000 µm, about 50 µm to about 500 µm, or about 100 µm to about 300 µm.

The discontinuities in the hydrophobic layer can be formed by any suitable method. For example, the discontinuities can be formed using techniques known for use on textiles, films, and coatings, such as embossing, patterning, foaming, spraying, stretching, and the like. In each case, the technique is applied in such a way as to produce discontinuities or voids in the hydrophobic layer. For example, when the hydrophobic layer is formed from a chemical foamed onto the surface of the fluid transport layer, the chemical can be foamed in such a way that the collapsed foam leaves discontinuities or voids in the coating that forms on the surface of the fluid transport layer. The discontinuities can also be formed by embossing a pattern in the material forming the hydrophobic layer as described, for example, in U.S. Pat. No. 3,459,618 (Egler). Additionally, when the hydrophobic layer is formed from a chemical that is applied to the surface of fluid transport layer, the chemical can be applied to or printed onto the fluid transport layer in a pattern that provides a plurality of discontinuities in the resulting chemical coating.

Figure 3:
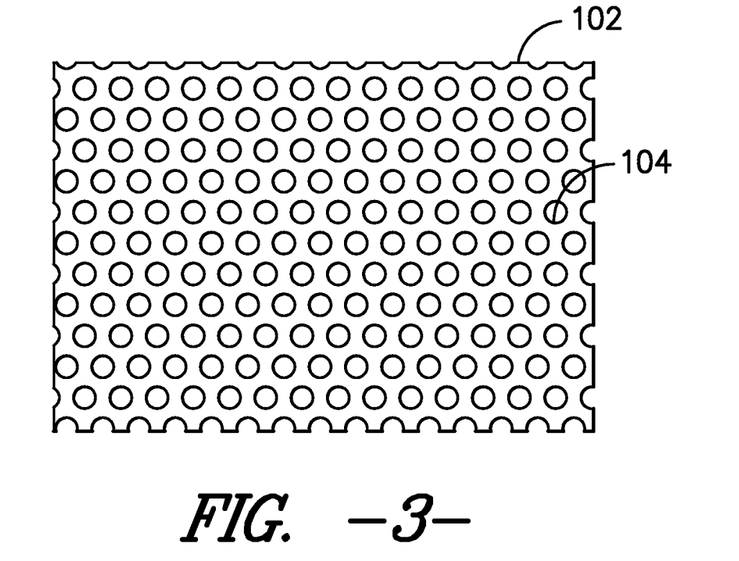
FIG. 3 is a plan view of an apertured polymeric film, such as that depicted in FIGS. 1 and 1A, suitable for use as the hydrophobic layer of a composite article according to the invention.

As noted above and depicted in FIG. 1 and FIG. 1A, the hydrophobic layer 102 can be an apertured film positioned so that it is adjacent to the first surface 108 of the fluid transport layer 106. Such an apertured film, which is depicted in FIG. 3, can be comprised of any suitable material. In certain embodiments, the apertured film can be comprised of a material having a surface energy that is lower than the surface energy of the first surface of the fluid transport layer. In such an embodiment, the apertures provided in the film allow fluid to pass through the apertured film and into the fluid transport layer, while the relatively low surface energy exhibited by the film establishes a surface energy gradient that functions to transport or pump fluid away from the apertured film and through the fluid transport layer. In a specific embodiment, the apertured film can be made from a polymer selected from the group consisting of polyolefins, polyesters, and polyamides. In certain embodiments, the apertured film can be a polyolefin film (e.g., polyethylene film), such as the Delnet® apertured polyethylene films available from DelStar Technologies, Inc. The apertures in the apertured film can be of any suitable size and shape, provided the apertures allow fluid to pass through the apertured film and into the fluid transport layer. For example, the apertured film can comprise apertures provided in the shape of slits, circles, hexagons, triangles, and the like.

Figure 4:
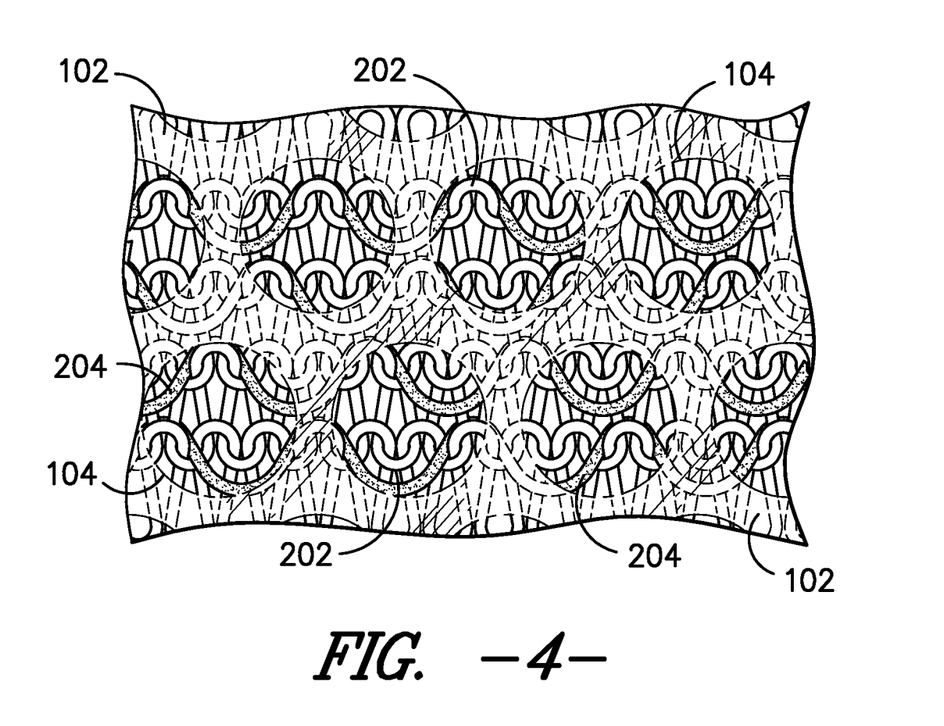
FIG. 4 is a plan view of a composite article according to the invention showing the surface of the composite article having the hydrophobic layer and the underlying fluid transport layer.

As noted above, FIG. 4 is a plan view of a composite article according to the invention having a hydrophobic layer, such as an apertured polymeric film described above, applied to a fluid transport layer, such as the textile material depicted in FIG. 2 and described above. As can be seen in FIG. 4, the hydrophobic layer 102 comprises a plurality of discrete discontinuities 104. These discontinuities preferably have a dimension sufficient to permit the passage of fluid through the hydrophobic layer 102 to the underlying fluid transport layer formed by the yarn(s) 202 and the effect yarn(s) 204. As noted above, the hydrophobic layer preferably exhibits a surface energy that is lower than the surface energy of the first surface of the fluid transport layer. Thus, in the embodiment depicted in FIG. 4, the hydrophobic layer 102 preferably exhibits a surface energy that is lower than the surface energy exhibited by the technical back of the fabric formed by the interlooped yarn(s) 202 and the laid-in effect yarn(s) 204. In such an embodiment, as fluid passes through the discontinuities in the hydrophobic layer, the difference in surface energies between the hydrophobic layer, the technical back of the fabric (i.e., the face of the fabric having a higher proportion of the effect yarn(s) 204), and the technical face of the fabric acts to transport or pump the fluid through the fluid transport layer and away from the fluid-contacting surface of the composite article.

Figure 5:
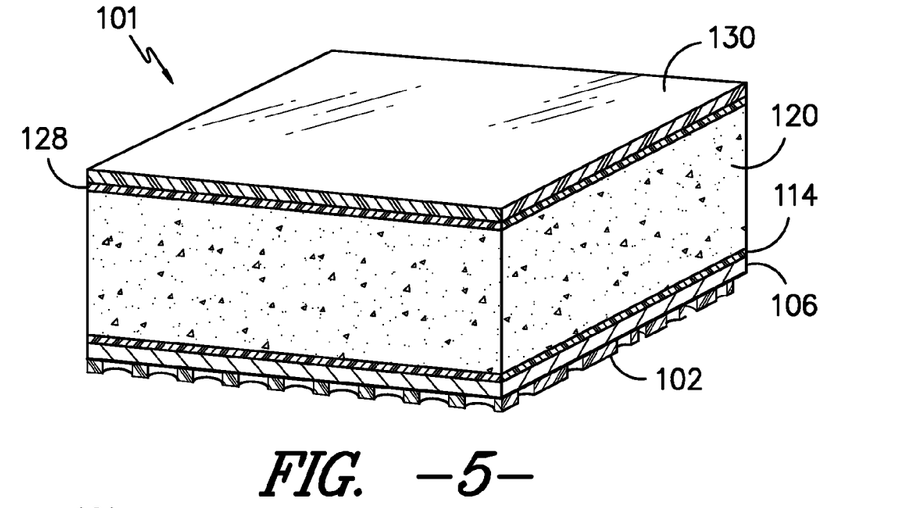
FIG. 5 is a perspective view of a composite article according to the invention having a fluid retentive layer and a moisture vapor permeable film.
Figure 5A:
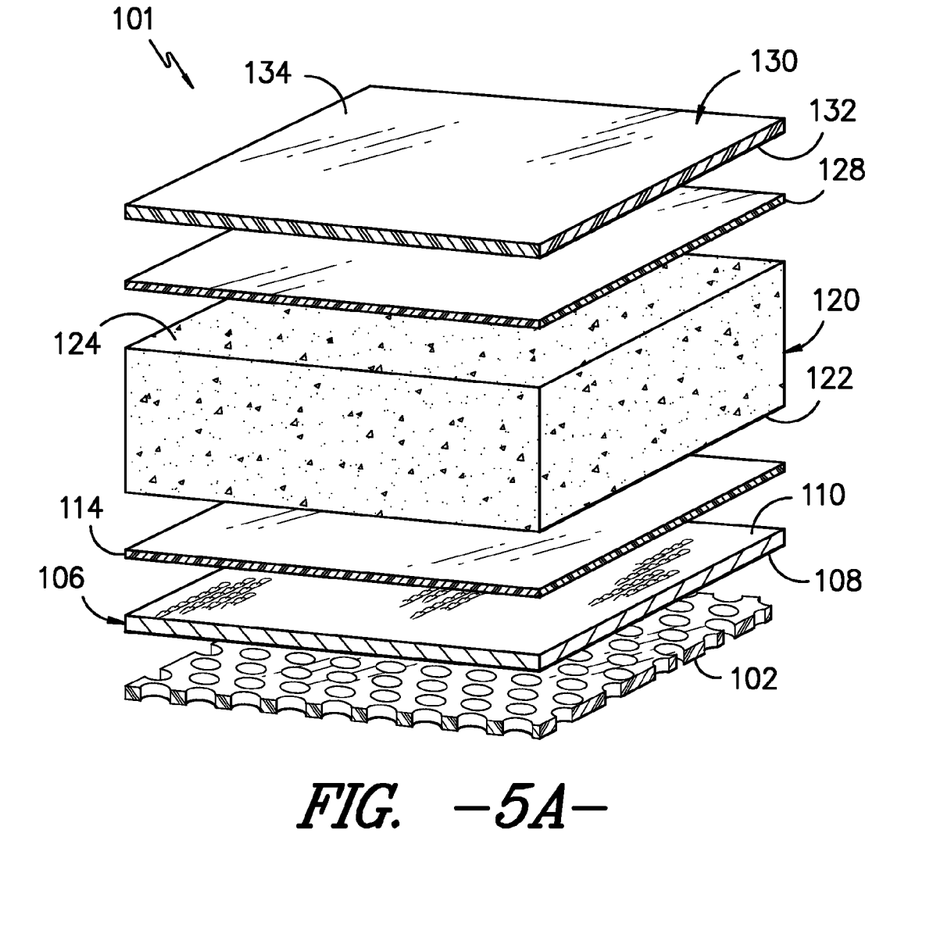
FIG. 5A is an exploded perspective view of the composite article depicted in FIG. 5.

As depicted in FIGS. 5 and 5A, the composite article 101 of the invention can further comprise a fluid retentive layer 120. The fluid retentive layer 120 of the composite article 101 can be any suitable material that is capable of retaining or absorbing fluids transported to the surface of the fluid retentive layer by the fluid transport layer. For example, the fluid retentive layer can be selected from the group consisting of foams, textile materials (e.g. woven, knit, and nonwoven textile materials), alginates, superabsorbent polymers, hydrocolloids, gels (e.g., hydrogels), and combinations or mixtures thereof. The fluid retentive layer can also comprise a combination of two or more discrete layers, which layers can comprise any of the absorptive materials listed above. In a specific embodiment, the fluid retentive layer 120 can be a foam, such as an open cell, non-reticulated polymer foam. Such foams can be made from any suitable material including, but not limited to, polyurethane polymers. In order to provide a fluid retentive layer exhibiting the requisite surface energy (i.e., a surface energy that is higher than the surface energy of the adjacent surface of the fluid transport layer), a polyurethane polymer used in making such a foam can be a polyester-based polyurethane polymer (i.e., a polyurethane polymer made from a reaction mixture containing a polyester polyol).

The fluid retentive layer 120 has a first surface 122 and second surface 124 and is positioned so that the first surface 122 is adjacent to the second surface 110 of the fluid transport layer 106. Thus, the fluid retentive layer 120 can act as a reservoir for the fluids taken up by the fluid transport layer 106. The composite article 101 can also comprise a moisture vapor permeable film 130, which is positioned so that it is adjacent to the second surface 124 of the fluid retentive layer 120. As depicted in FIG. 5 and FIG. 5A, the fluid transport layer, fluid retentive layer, and, if present, moisture vapor permeable film can be attached to each other using adhesive layers 114, 128.

The fluid retentive layer of the composite article can exhibit any suitable absorptive capacity. For example, the fluid retentive layer can exhibit a fluid absorption of about 100 wt. % or more based on the weight of the fluid retentive layer. In a specific embodiment, the fluid retentive layer can exhibit a fluid absorption of about 200 wt. % or more, about 300 wt. % or more, about 400 wt. % or more, about 500 wt. % or more, about 600 wt. % or more, about 700 wt. % or more, about 800 wt. % or more, about 900 wt. % or more, or about 1000 wt. % or more based on the weight of the fluid retentive layer. The absorptive capacity of the fluid retentive layer can be measured by any suitable means. For example, the absorptive capacity of the fluid retentive layer can be measured by immersing a known weight of the fluid retentive layer in phosphate-buffered saline containing 0.9 wt. % sodium chloride at 37° C. for 30 minutes.

As noted above and depicted in FIG. 5 and FIG. 5A, the fluid retentive layer 120 comprises a first surface 122 and is positioned so that the first surface 122 is adjacent to the second surface 110 of the fluid transport layer 106. The first surface 122 of the fluid retentive layer 120 exhibits a surface energy. In order to facilitate the transport of aqueous fluids from the fluid transport layer 106 to the fluid retentive layer 120, the surface energy of the first surface 122 of the fluid retentive layer 120 can be greater than the surface energy of the second surface 110 of the fluid transport layer 106. By utilizing a fluid retentive layer 120 having a surface energy that is greater than the surface energy of the second surface 110 of the fluid transport layer 106, the fluid retentive layer 120 exhibits a greater affinity for aqueous fluids than the fluid transport layer 106. The resulting composite therefore is capable of transporting fluid from the fluid transport layer 106 to the fluid retentive layer 120. Moreover, due to the difference in surface energies and affinity for aqueous fluids, such an embodiment of the composite article is capable of transporting this fluid below the saturation point of the fluid transport layer (i.e., before the fluid transport layer becomes saturated with the fluid). Thus, when such a composite article is used as a wound dressing, this ability can significantly reduce the risk of maceration associated with exuding wounds.

In such embodiments of the composite article of the invention, the difference between the surface energy of the first surface 122 of the fluid retentive layer 120 and the second surface 110 of the fluid transport layer 106 can be of any suitable magnitude. For example, the surface energy of the first surface 122 of the fluid retentive layer 120 can be about 105% or more of the surface energy of the second surface 110 of the fluid transport layer 106. In a specific embodiment, the surface energy of the first surface 122 of the fluid retentive layer 120 can be about 110% or more, about 115% or more, about 120% or more, or about 125% or more of the surface energy of the second surface 110 of the fluid transport layer 106.

As noted above and depicted in FIG. 5 and FIG. 5A, the composite article 101 can further comprise a moisture vapor permeable film 130. When present, the moisture vapor permeable film 130 is positioned so that the first surface 132 of the moisture vapor permeable film 130 is adjacent to the second surface 124 of the fluid retentive layer 120. In the embodiment depicted in FIG. 5 and FIG. 5A, the second surface 132 of the moisture vapor permeable film 130 provides a top, occlusive surface for the composite article 101 that helps to prevent foreign matter (e.g., fluids, dirt, microbes, etc.) from entering the composite article.

The moisture vapor permeable film can be any suitable material that is permeable to water vapor and capable of providing the occlusive surface noted above. The moisture vapor permeable film can be selected from polyurethane films, polyamide block copolymer films, and polyester block copolymer films. In a specific embodiment, the moisture vapor permeable film can be a polyurethane film, such as a polyether-based polyurethane film or polyester-based polyurethane film.

The moisture vapor permeable film can have any suitable moisture vapor transmission rate (MVTR). More specifically, the moisture vapor permeable film typically exhibits an MVTR that is high enough to prevent the composite article from becoming saturated when it is placed in contact with, for example, a moderately-exuding wound. However, the moisture permeable film typically does not exhibit an MVTR that is so high that the composite article will be completely dry when it is placed in contact with, for example, a lightly-exuding or non-exuding wound. In a specific embodiment, the moisture vapor permeable film exhibits an MVTR of about 500 g/m$^2$/24 hr or more, about 1,000 g/m$^2$/24 hr or more, about 5,000 g/m$^2$/24 hr or more, or about 10,000 g/m$^2$/

24 hr or more (e.g., about 12,000 g/m²/24 hr), when measured in accordance with ASTM Standard E-96 entitled "Standard Test Methods for Water Vapor Transmission of Materials" using an upright cup method.

As depicted in FIG. 5 and FIG. 5A, the adjacent surfaces of the fluid transport layer 106 and, when present, the fluid retentive layer 120, and the moisture vapor permeable film 130 can be adhered to each other using one or more suitable adhesives 114,128. In such an embodiment, the adhesives help to provide a coherent, dimensionally stable composite article and prevent delamination of the layers upon removal of the composite article. The adhesive(s) used to adhere adjacent surfaces of the fluid transport layer, the fluid retentive layer, and the moisture vapor permeable film of the composite can be any suitable adhesive(s). Adhesives suitable for adhering adjacent surfaces of the fluid transport layer, the fluid retentive layer, and the moisture vapor permeable film include, but are not limited to, solvent-based adhesives, latex adhesives, pressure-sensitive adhesives, hot-melt adhesives, and reactive adhesives. Suitable pressure-sensitive adhesives include, but are not limited to, pressure-sensitive adhesives made from acrylics, natural latexes, styrene-butadiene rubbers, and reclaimed rubbers. Suitable hot-melt adhesives include, but are not limited to, polyamides, polyolefins, and poly(ethylene-co-vinyl acetate).

As noted above, the adhesive layers 114,128 can be any suitable adhesive. In a specific embodiment, the adhesive layer 114 can be a hot-melt adhesive, such as those hot-melt adhesives listed in the foregoing paragraph. In a more specific embodiment, the adhesive layer 114 can be a polyamide hot-melt adhesive. In order to ensure that the adhesive layer 114 does not act as an occlusive layer preventing the transport of fluid from the fluid transport layer 106 to the fluid retentive layer 120, the adhesive comprising the adhesive layer 114 can be applied in a pattern covering only a portion of the area between the adjacent surfaces of the fluid transport layer 106 and the fluid retentive layer 120. The amount of coverage provided by the adhesive can be any suitable amount that provides sufficient adhesion of the fluid transport layer 106 and the fluid retentive layer 120 (i.e., sufficient adhesion to prevent delamination of the layers during use of the composite article) without preventing the transport of fluid between the two layers. For example, the adhesive 114 can be provided in a suitable pattern covering about 10% to about 98% of the area between the fluid transport layer 106 and the fluid retentive layer 120. In a specific embodiment, the adhesive 114 can be a polyamide hot-melt adhesive web providing, for example, about 10% to about 98% coverage of the area between the fluid transport layer 106 and the fluid retentive layer 120.

When present, the adhesive can be applied to the layers of the composite article in any suitable amount. The adhesive typically is present in or applied to the composite article in an amount sufficient to prevent partial or complete delamination of the layers of the composite article without negatively impacting the fluid transport properties of the composite article. Also, the amount of adhesive required to provide a composite article having the desired physical properties may vary based upon the particular adhesive(s) used. In a specific embodiment, such as when the adhesive is a hot-melt adhesive (e.g., a polyamide hot-melt adhesive), the adhesive can be present in the composite article in an amount of about 3 g/m² or more (about 0.1 oz/yd² or more), about 17 g/m² or more (about 0.5 oz/yd² or more), about 34 g/m² or more (about 1 oz/yd² or more), about 50 g/m² or more (about 1.5 oz/yd² or more), about 100 g/m² or more (about 3 oz/yd² or more), or about 340 g/m² or more (about 10 oz/yd² or more).

In a specific embodiment, the adhesive layer 128 between the fluid retentive layer 120 and the moisture vapor permeable film 138 can be a pressure-sensitive adhesive, such as those pressure-sensitive adhesives listed in the preceding paragraphs. In a more specific embodiment, the adhesive layer 128 is an acrylic pressure-sensitive adhesive. As with the adhesive layer 114 between the fluid transport layer 106 and the fluid retentive layer 120, the adhesive comprising the adhesive layer 128 can be applied in a pattern covering only a portion of the area between the adjacent surfaces of the fluid retentive layer 120 and the moisture vapor permeable film 130. Once again, the amount of adhesive applied should be sufficient to prevent delamination of the fluid retentive layer 120 and the moisture vapor permeable film 130 without preventing the transmission of moisture vapor through the moisture vapor permeable film 130.

In an alternative embodiment, the moisture vapor permeable film 130 can be laminated onto the second surface 124 of the fluid retentive layer 120. In such an embodiment, the moisture vapor permeable film can be laminated onto the fluid retentive layer by heating the film to a temperature sufficient to at least partially melt the polymer(s) from which it is made, pressing the film onto the fluid retentive layer, and then allowing the film to cool to a temperature sufficient for the polymer(s) from which the film is made to solidify. In this embodiment, the heated film should be pressed onto the fluid retentive layer using a pressure sufficient to ensure that physical bonds between the film and fluid retentive layer are formed once the film cools and solidifies.

The composite article can further comprise one or more active ingredients. These active ingredients can be incorporated into one or more of the layers of the composite article, or they can be applied as a surface coating on or between one or more of the layers of the composite article. Actives suitable for use in the composite article include, but are not limited to, antimicrobial agents, antibiotics, analgesics, moisturizers (e.g., glycerin, urea, lactic acid, etc.), humectants, debriders (e.g., enzymatic debriders), matrix metalloproteinase inhibitors, growth factors, and combinations thereof. Suitable antimicrobial agents include, but are not limited to, silver-based antimicrobials, such as silver ion exchange materials (e.g., silver zirconium phosphates, silver calcium phosphates, silver zeolites, etc.), silver particles (e.g., metallic silver, nanosilver, colloidal silver, etc.), silver salts (e.g., AgCl, $Ag_2CO_3$, etc.), silver glass, and combinations thereof. In a specific embodiment, the antimicrobial agent can be a silver ion exchange material such as a silver sodium hydrogen zirconium phosphate. Suitable antimicrobial agents also include, but are not limited to, antimicrobial compounds containing copper, zinc, iodine, 5-chloro-2-(2,4-dichlorophenoxy)phenol), polyhexamethylene biguanide (PHMB), N-halamines, chlorhexidine, quaternary ammonium complexes, and combinations and mixtures thereof. Antimicrobial agents suitable for use in the composite article also include combinations of silver-based antimicrobials (e.g., silver ion exchange materials) and non-silver-based antimicrobials.

In order to actively mitigate the risk of infection when the composite is used as a wound dressing, the fluid transport layer 102 can, in a specific embodiment, comprise one or more antimicrobial agents. The antimicrobial agent(s) can be incorporated into the material forming the fluid transport layer. For example, when the fluid transport layer is a textile material such as that depicted in FIG. 2, the antimicrobial agent(s) can be incorporated into the fibers or yarns forming the textile material. Alternatively, the antimicrobial agent(s) can be applied to the fluid transport layer in the form of a coating. In a specific embodiment, the fluid transport layer can comprise a coating applied to one or more surfaces of the fluid transport layer, the coating comprising one or more antimicrobial agents and a suitable binder. For the sake of clarity, such a coating is different from and in addition to any hydrophobic coating applied to the fluid transport layer in order to provide the hydrophobic layer of the composite article. The binder used in such a coating can be any suitable binder, such as a polyurethane binder. In a more specific embodiment, the fluid transport layer can be a textile material such as that depicted in FIG. 2 further comprising a coating applied to both surfaces of the textile material. In such an embodiment, the coating can comprise a polyurethane binder and a silver-based antimicrobial, such as a silver sodium hydrogen zirconium phosphate.

In those embodiments of the composite incorporating a silver-based antimicrobial, the antimicrobial can be applied to the fluid transport layer in any suitable amount. As will be understood by those of ordinary skill in the art, the suitable amount of silver-based antimicrobial can depend upon several factors, such as the particular type of silver-based antimicrobial used. Different silver-based antimicrobials generally contain different levels of ionic silver, which is the antimicrobially-active component of silver-based antimicrobials. Thus, those silver-based antimicrobials containing a low amount of ionic silver per unit of weight of the antimicrobial typically will be applied at higher loadings than silver-based antimicrobials containing a higher amount of ionic silver per unit of weight of the antimicrobial. In certain embodiments, the antimicrobial can be applied to the fluid transport layer in an amount sufficient to provide about 0.001 wt. % or more, about 0.005 wt. % or more, or about 0.007 wt. % or more of silver (e.g., about 0.0076 wt. % or more of silver) based on the weight of the fluid transport layer. Alternatively or additionally, the antimicrobial can be applied to the fluid transport layer in an amount sufficient to provide about 60 wt. % or less, about 25 wt. % or less, about 8 wt. % or less, or about 3.5 wt. % or less of silver (e.g., about 2 wt. % or less of silver) based on the weight of the fluid transport layer. The aforementioned minima and maxima can be combined as appropriate to yield an appropriate range for the amount of antimicrobial used. Accordingly, in certain embodiments, the antimicrobial can be applied to the fluid transport layer in an amount sufficient to provide about 0.001 to about 60 wt. % of silver (e.g., about 0.0076 to about 2 wt. % of silver) based on the weight of the fluid transport layer. In those embodiments using a polyurethane binder, the binder can be applied in an amount of about 0.2 to about 7 wt. % (e.g., about 2 to about 6 wt. %) based on the weight of the fluid transport layer.

In another embodiment, one or more antimicrobial agents can be applied to or incorporated into the fluid retentive layer. For example, when the fluid retentive layer is a polymer foam, one or more suitable antimicrobial agents can be incorporated into the reaction mixture used to form the polymer foam, thereby providing a polymer foam having the antimicrobial agent(s) incorporated throughout the polymer foam. In a specific embodiment, the fluid retentive layer 120 can be a polymer foam (e.g., a polyether-based polyurethane foam) comprising a silver-based antimicrobial agent (e.g., a silver sodium hydrogen zirconium phosphate antimicrobial) dispersed or incorporated throughout the polymer foam.

In those embodiments of the composite article in which the hydrophobic layer does not exhibit adhesive properties, the composite article can comprise a layer of adhesive on the fluid-contacting surface of the composite article (i.e., the surface of the hydrophobic layer opposite the fluid transport layer) in order to secure the composite article in place during use. The adhesive can be applied over the entire area of the fluid-contacting surface of the composite article, or the adhesive layer can be applied to only a portion of the area. For example, the adhesive can be applied to the perimeter of the composite article, thereby providing a means for the composite article to be adhered to the surface (e.g., skin) without materially affecting the fluid transport properties of the bulk of the composite article. The adhesives suitable for use in such a composite article include, but are not limited to, the pressure-sensitive adhesives described above in the discussion of the adhesive layers 114,128.

While the composite articles in FIGS. 1, 1A, 5, and 5A have been depicted as comprising layers that are coextensive with adjacent layers, the layers need not be coextensive, provided they are arranged as described above. In one embodiment, for example, the moisture vapor permeable film can have a greater area than the fluid transport layer and the fluid retentive layer. Such a composite article would comprise an "excess" of the moisture vapor permeable film extending beyond the perimeter of the fluid transport layer and the fluid retentive layer. Further, this "excess" can, in certain embodiments, be coated with a pressure-sensitive adhesive (such as those described above) in order to provide a means for the composite article to be secured in place during use. Additionally, the composite article can, in certain embodiments, comprise an additional layer (e.g., a film or textile layer) overlying the moisture vapor permeable film, which additional layer has a greater area than the underlying moisture vapor permeable film. The "excess" of the additional layer can, in certain embodiments, be coated with a suitable adhesive (e.g., a pressure-sensitive adhesive, such as those described above) in order to provide a means for the composite article to be secured in place during use. In another embodiment, the fluid retentive layer can comprise a plurality of discrete, non-continuous "islands" positioned between the fluid transport layer and the moisture vapor permeable film. These "islands" can be formed from any of the materials listed in the discussion of the fluid retentive layer, including polymer foams.

The composite article can be provided in any shape or form suitable for its intended use. For example, the composite article can be provided in the shape of a rectangle, square, circle, heart, or butterfly in order to provide an article suitable for use in dressing a particular wound or location of wound. Furthermore, the perimeter of the composite article can be tapered so that the profile of the composite article is thinner at its perimeter. This embodiment of the composite article can be produced, for example, by using a fluid retentive layer having a thinner profile at its perimeter. Such a composite article would provide a less harsh profile when used as a wound dressing, which should increase patient comfort.

The composite article of the invention can be provided in any suitable dimensions. For ease of wear and patient comfort when used as a wound dressing, the composite article typically is about 1 cm or less in thickness, preferably about 50 mm or less in thickness. In order to provide an article that is capable of managing a moderate amount of fluid (e.g., wound exudates), the composite article typically is about 0.5 mm or more in thickness. In a specific embodiment, the composite article is from about 1 mm to about 20 mm in thickness, or from about 5 mm to about 10 mm (e.g., about 5 mm to about 8 mm) in thickness.

As noted throughout this specification, the composite article of the invention is believed to be particularly well-suited for use as a wound dressing. Thus, in a second embodiment, the invention provides a wound dressing having the structure described above for the first embodiment of the composite article of the invention. When used as a wound dressing, the composite article typically is positioned so that the hydrophobic layer is adjacent to the skin of the patient. When this surface of the composite article exhibits a lower surface energy than the fluid transport layer and, if present, the fluid retentive layer, the aqueous fluids (e.g., wound exudate or perspiration) contacting the hydrophobic layer will be transported from the hydrophobic layer to fluid transport layer and, if present, into the fluid retentive layer. Also, as noted above, such a gradient of surface energies among the layers of the composite article allows these aqueous fluids to be transported from one layer to the adjacent layer before the layer becomes saturated. Thus, for example, the difference in surface energies between the layers allows the aqueous fluids to be transported from the fluid retentive layer before the fluid transport layer becomes saturated. Once in the fluid transport layer or fluid retentive layer, the aqueous fluids can then evaporate, for example, through the moisture vapor permeable film. It is believed that these active fluid management properties provide a wound dressing that is capable of maintaining an environment that is sufficiently moist to promote wound healing while also maintaining an environment that is not so moist as to cause maceration of the skin and the proliferation of bacteria.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A composite article comprising:
   (a) a fluid transport layer, the fluid transport layer having a first surface and a second surface, the first surface of the fluid transport layer having a first surface energy, and the second surface of the fluid transport layer having a second surface energy, the second surface energy being greater than the first surface energy, and
   (b) a hydrophobic layer applied to the first surface of the fluid transport layer, the hydrophobic layer having a third surface energy, the third surface energy being less than the first surface energy, the hydrophobic layer comprising a plurality of discontinuities, at least a portion of the discontinuities having a dimension sufficient to permit the passage of fluid through the hydrophobic layer and into the fluid transport layer,
   wherein the fluid transport layer is a jersey knit textile material comprising a first yarn forming a plurality of interlocking loops and at least one effect yarn tucked into the interlocking loops formed by the first yarn, wherein the plurality of interlocking loops formed by the first yarn provide the second surface of the fluid transport layer, and wherein the first yarn is more hydrophilic than the effect yarn.

2. The composite article of claim 1, wherein the first yarn comprises a polyamide and the effect yarn comprises a polyester.

3. The composite article of claim 2, wherein the fluid transport layer further comprises one or more elastomeric yarns.

4. The composite article of claim 1, wherein the hydrophobic layer comprises a material selected from the group consisting of apertured polymeric films, fluorochemicals, hydrophobic, pressure sensitive adhesives, waxy compounds, silicones, hydrophobic acrylic polymers, polyvinyl chloride-based polymers, and combinations thereof.

5. The composite article of claim 4, wherein the hydrophobic layer comprises an apertured polymeric film.

6. The composite article of claim 4, wherein the hydrophobic layer comprises a fluorochemical.

7. The composite article of claim 4, wherein the hydrophobic layer comprises a hydrophobic, pressure sensitive adhesive.

8. The composite article of claim 4, wherein the hydrophobic layer comprises a waxy compound.

9. The composite article of claim 4, wherein the hydrophobic layer comprises a silicone.

10. The composite article of claim 4, wherein the hydrophobic layer comprises a hydrophobic acrylic polymer.

11. The composite article of claim 1, wherein the hydrophobic layer comprises a plurality of discontinuities having a dimension of from about 7 μm to about 3,000 μm.

12. The composite article of claim 11, wherein the hydrophobic layer comprises a plurality of discontinuities having a dimension of from about 50 μm to about 500 μm.

13. The composite article of claim 11, wherein the hydrophobic layer comprises a plurality of discontinuities having a dimension of from about 100 μm to about 300 μm.

14. The composite article of claim 1, wherein the composite article further comprises a moisture vapor permeable film, the moisture vapor permeable film being positioned so that it is adjacent to the second surface of the fluid transport layer.

15. The composite article of claim 14, wherein the moisture vapor permeable film is a polyurethane film comprising a polyurethane polymer selected from the group consisting of polyether-based polyurethanes, polyester-based polyurethanes, and combinations thereof.

16. The composite article of claim 14, wherein the moisture vapor permeable film exhibits a moisture vapor transmission rate (MVTR) of about 500 g/m$^2$/24 hr or more.

17. The composite article of claim 1, wherein the composite article further comprises a fluid retentive layer, the fluid retentive layer having a first surface and a second surface, the first surface of the fluid retentive layer having a fourth surface energy, the fourth surface energy being greater than the second surface energy, and the fluid retentive layer being positioned so that the first surface of the fluid retentive layer is adjacent to the second surface of the fluid transport layer.

18. The composite article of claim 17, wherein the fluid retentive layer is selected from the group consisting of foams, textile materials, alginates, superabsorbent polymers, gels, hydrocolloids, and combinations thereof.

19. The composite article of claim 18, wherein the fluid retentive layer comprises a polyester-based polyurethane foam.

20. The composite article of claim 17, wherein the composite article further comprises a moisture vapor permeable film, the moisture vapor permeable film being positioned so that it is adjacent to the second surface of the fluid retentive layer.

21. The composite article of claim 20, wherein the moisture vapor permeable film is a polyurethane film comprising a polyurethane polymer selected from the group consisting of polyether-based polyurethanes, polyester-based polyurethanes, and combinations thereof.

22. The composite article of claim 21, wherein the moisture vapor permeable film exhibits a moisture vapor transmission rate (MVTR) of about 500 g/m$^2$/24 hr or more.

* * * * *